United States Patent [19]

Okamoto et al.

[11] Patent Number: 5,004,735
[45] Date of Patent: Apr. 2, 1991

[54] PHARMACEUTICAL COMPOSITIONS FOR THE INHIBITION OF TUMOR METASTASIS

[75] Inventors: Yasushi Okamoto, Tokyo; Yoshiyuki Tahara; Yoshio Mishima, both of Saitama, all of Japan

[73] Assignee: Nisshin Flour Milling Co., Ltd., Tokyo, Japan

[21] Appl. No.: 373,909

[22] Filed: Jun. 29, 1989

[30] Foreign Application Priority Data

Jul. 13, 1988 [JP] Japan .................. 63-172638

[51] Int. Cl.$^5$ ............... A61K 31/66; A61K 31/045
[52] U.S. Cl. .................. 514/134; 514/739; 514/937
[58] Field of Search ............ 514/134, 739, 75, 560, 514/671, 437

[56] References Cited

FOREIGN PATENT DOCUMENTS 39521 8/1987 Japan .

OTHER PUBLICATIONS

B-1-6 Branching of ASn-Linked Oligosaccharides is Directly Associated with Metastasis, Dennis et al., Science, 236, 582-585, 1987.
Stimulation of Protein Glycosylation in Cultured Hepatoma Cells by Polyprenyl Compounds, Okamoto et al., GANN 76, 760-770, 1985.
Enhancement of Chemotherapeutic Effect on Lymph Node Metastasis by Anticancer Agents in Fat Emulsion.
Takahashi et al, Chem. Abstract 126307r, 1978.
Dennis et al., Science, 236, 582-585 (May 1, 1987).
Okamoto et al., JPN. J. Cancer Res., (Gann.) 76, 760-770 (1985).

*Primary Examiner*—Thurman K. Page
*Assistant Examiner*—G. S. Kishore
*Attorney, Agent, or Firm*—Abelman Frayne Rezac & Schwab

[57] ABSTRACT

Polyprenols and polyprenyl phosphates are of the formula

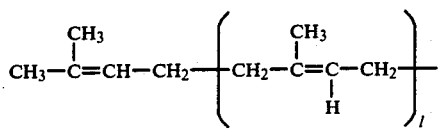

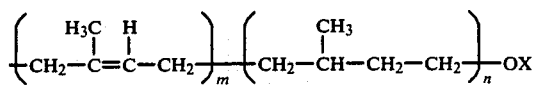

wherein

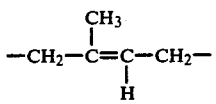

represents a trans-isoprene unit,

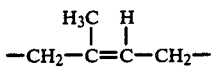

represents a cis-isoprene unit,

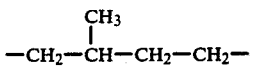

represents a dihydroisoprene unit, l is an integer of 2 to 8, m is 0 or an integer of 5 to 18, n is 0 or 1, the sum of l and m is in the range of 8 to 20, and X represents a hydrogen atom or —PO$_3$MM' wherein M and M' may be the same or different and each is a hydrogen atom or a monovalent cation or both M and M' together form a divalent cation. They are useful as a medicament for the inhibition of tumor metastasis.

8 Claims, No Drawings

PHARMACEUTICAL COMPOSITIONS FOR THE INHIBITION OF TUMOR METASTASIS

FIELD OF THE INVENTION

This invention relates to polyprenols and polyprenyl phosphates having their uses as a medicament for the inhibition of tumor metastasis.

BACKGROUND OF THE INVENTION

A variety of methods for the treatment of tumors have hitherto been attempted, including surgical operation, radiotherapy, physiotherapy such as thermatology and chemotherapy, alone or in combinations. In particular, surgical operation and radiotherapy are highly effective in removing primary tumors. Even if, however, an earlier detection of a primary tumor and the removal thereof by surgical operation are successful, the possible metastasis of the tumor may often bring about death of the patient. Furthermore, tumors in organs or regions where surgical operation is impossible can only be treated by means of physiotherapy or chemotherapy. In such case, possible metastatic tumors in other regions of the body may often lead to death of the patient, even if growth of the primary tumor is successfully inhibited. Thus, one of the most difficult problems in tumor treatment is to inhibit metastasis.

The metastatic process of tumor consists of several steps including release of cells from primary tumors, transfer thereof via vessels, adhesion to the other organs, and infiltration and proliferation of the tumor cells therein. The defense mechanism of organism participates in said steps. Recently, complex mechanism of tumor metastasis has partly been elucidated but the total mechanism has not been clarified.

Many studies have been made on development of medicaments for inhibiting tumor metastasis, with little successful results.

The mechanism of tumor metastasis is complicated and has not clarified completely. However, the relation between metastatic potential of tumor cells and structure of N-glycosidically linked saccharide chain on cell surface have been investigated relatively well and some important findings have been obtained. It was known that most of tumor cells have increased branching in N-glycosidically linked saccharide chain on cell surface in comparison with normal cells, and that such increase is due to the increase in the special GlcNAc$\beta$1-6Man structure (wherein GlcNAc stands for N-acetyl glucosamine and Man stands for mannose) in the saccharide chain. Recently, James W. Dennis et al. (Science Vol. 236, 582-585, May 1987) has reported that the presence of GlcNAc$\beta$1-6Man structure is directly associated with the metastatic potential of tumor cells, and the tumor cells having more such structure exhibit higher metastatic potential.

The increase and decrease in GlcNAc$\beta$1-6Man structure on the tumor cell surface can be determined using L-PHA, a kind of lectin. L-PHA binds specifically to saccharide chains containing GlcNAc$\beta$1-6Man structure and inhibits the proliferation of the cells depending upon the amount of said structure present (Science Vol. 236, 582-585, May 1987). Therefore, the increase and decrease in GlcNAc$\beta$1-6Man structure can be determined by measuring the L-PHA sensitivity (susceptibility to inhibition of proliferation by L-PHA) of the specific tumor cells.

We have investigated the effect of many compounds on L-PHA sensitivity of tumor cells utilizing the above mentioned properties of tumor cells, and found that polyprenols and polyprenyl phosphates permit the reduction in L-PHA sensitivity of tumor cells, i.e., the reduction in GlcNAc$\beta$1-6Man structure. From these facts, we have found that polyprenols and polyprenyl phosphates can effectively inhibit tumor metastasis.

Some of polyprenols and polyprenyl phosphates are disclosed in Jpn. J. Cancer Res. (Gann), 76, 760–770, August 1985 and Japanese Patent LOP Publication No. 39521/1987. However, there is no reference to their pharmaceutical uses as a medicament for the inhibition of tumor metastasis.

The present invention results from efforts to develop a new use of polyprenols and polyprenyl phosphates for the inhibition of tumor metastasis.

DISCLOSURE OF THE INVENTION

This invention relates to pharmaceutical compositions for the inhibition of tumor metastasis in mammals comprising one or more of polyprenols and polyprenyl phosphates as an active ingredient, and methods of using them to inhibit tumor metastasis in mammals. The polyprenols and polyprenyl phosphates are of the formula

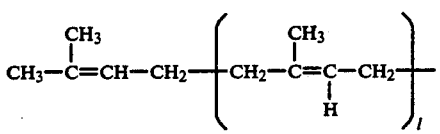

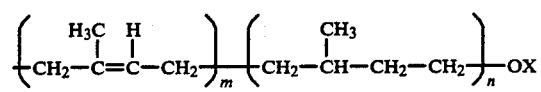

wherein

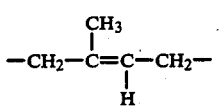

represents a trans-isoprene unit,

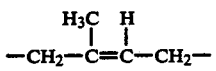

represents a cis-isoprene unit,

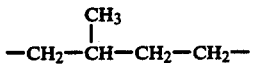

represents a dihydroisoprene unit, l is an integer of 2 to 8, m is 0 or an integer of 5 to 18, n is 0 or 1, the sum of l and m is in the range of 8 to 20, and X represents a hydrogen atom or —PO$_3$MM' wherein M and M' may be the same or different and each is a hydrogen atom or a monovalent cation (such as sodium, potassium, ammonium, etc.) or both M and M' together form a divalent cation (such as calcium, etc.).

Representative examples of the compounds represented by the above formula are given below.

Solanesyl phosphate diammonium salt (Compound A)

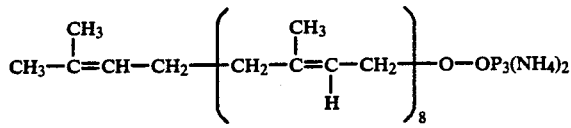

α-Dihydrodecaprenol (Compound B)

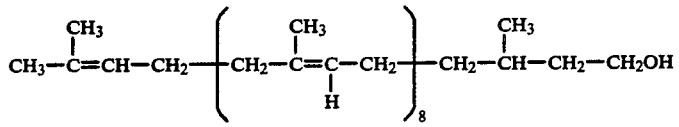

α-Dihydrodecaprenol phosphate diammonium salt (Compound C)

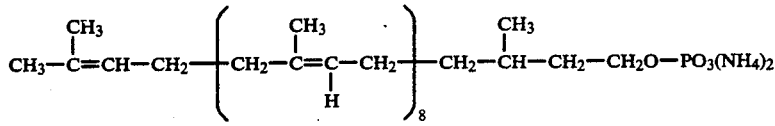

Mixed polyprenols having 45 to 60 carbons (Compound D)

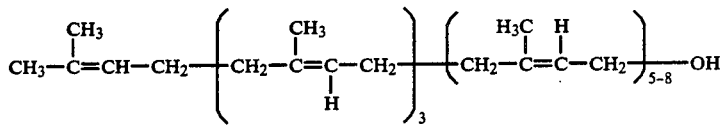

Mixed α-dihydropolyprenols having 50 to 65 carbons (Compound E)

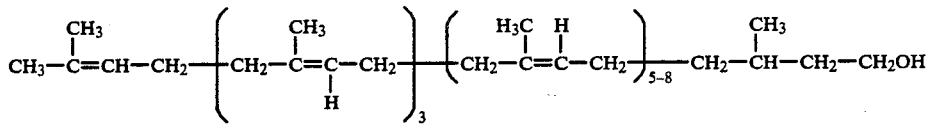

Mixed dolichyl phosphate diammonium salt having 75 to 110 carbons (Compound F)

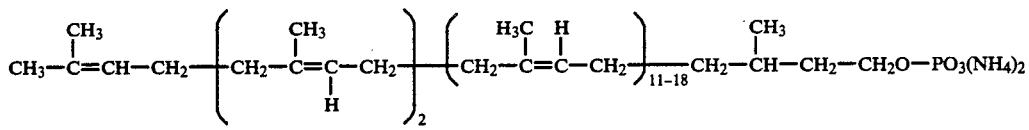

α-Dihydrodecaprenyl phosphate (Compound G)

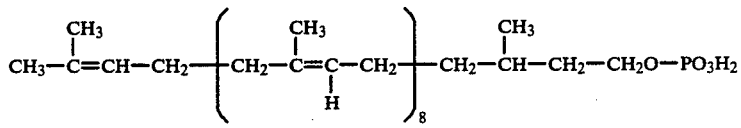

α-Dihydrodecaprenyl phosphate (Compound H)

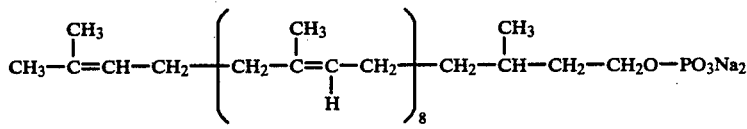

The compounds A, B and C of the invention can be prepared by the methods disclosed in Jpn. J. Cancer Res. (Gann), 76, 760-770, August, 1985 incorporated herein by reference.

The acute toxicity of these compounds are extremely low. For example, all of these compounds have $LD_{50}$ of more than 1 g/Kg when administered intraperitoneally to male ICR mice.

The polyprenols and polyprenyl phosphates of the invention can effectively inhibit metastasis of tumor cells in a mammal, as shown later in examples. For instance, an addition of one or more of the polyprenols and polyprenyl phosphates to a melanoma cell culture causes structural changes in the cell surface saccharide chain. The inhibitory effect of these compounds on tumor metastasis is presumed to exhibit through an effect on such cell surface structure.

The polyprenols and polyprenyl phosphates are useful for the inhibition of metastasis of various kinds of malignant tumors or cancers such as stomach cancer, esophageal cancer, small intestinal cancer, large intestinal cancer, rectal cancer, uterine cancer, bladder cancer, skin cancer, melanoma, hepatoma, pancreatoma, breast cancer, encephalophyma, lymphoma, etc. More particularly, the compounds of the present invention can inhibit hematogenous metastasis, which means a transfer of tumor cells in a mammal from a primary site to a distant one through the blood vessel. The primary sites include breast, lung, stomach, intestinum, liver, skin, brain, etc.

The polyprenols and polyprenyl phosphates of this invention can be administered to inhibit the metastasis of such malignant tumors or cancers as recited above, by any means that produces contact of the active agent with the site of action in the body of a mammal. They can be administered alone, but are generally administered with a pharmaceutical carrier selected on the basis of the chosen route of administration and standard pharmaceutical practice. They can be administered alone or in combination with other anti-tumor agents, or in association with other therapies, for example, surgical operation or physiotherapy such as radiotherapy. The compounds of the present invention may also be administered alone after such surgical operation, physiotherapy (for example, radiotherapy) or chemotherapy, in order to prevent metastasis of tumors. In any case, metastasis of tumor is significantly reduced with consequent prolongation of life.

The dosage administered will vary depending upon a mode and route of administration, age, sex and weight of patients, nature and extent of symptoms, kind of concurrent treatment, frequency of treatment, etc. Usually, a daily dose of active ingredient for adult human can be about 10 to 2000 milligrams per kilogram of body weight for oral administration and about 5 to 1000 mg/Kg or more for parenteral administration.

The active ingredients, i.e., polyprenols and polyprenyl phosphates may be administered orally or parenterally, for example, by intramuscular, subcutaneous or intravenous injection, in various dosage forms such as tablets, capsules, powders, solutions, emulsions, suspensions, etc.

An oily emulsion is a preferred pharmaceutical dosage form for administration of the compounds of this invention, because of its increased stability and extended applicability.

The oily emulsions may be prepared using, in addition to the active ingredient, physiologically acceptable oils such as soybean oil, etc., together with conventional auxiliaries such as emulsifiers, e.g., soybean lecithin, egg yolk lecithin; osmotic pressure adjusting agents such as glycerol; emulsifier aids such as aliphatic acids of 6–30 carbon atoms, salts and monoglycerides thereof to accelerate emulsification; and stabilizers such as cholesterol, tocopherol, albumin, polysaccharides and amide and ester derivatives of aliphatic acids to enhance storage stability.

The particles in the oily emulsions containing polyprenols or polyprenyl phosphates are finely divided and are not more than 300 nm in average particle diameter. The oily emulsions are extremely stable during storage. The oily emulsions, when administered to experimental animals, permit effective exertion of the pharmacological activity of the active ingredients. The oily emulsions may be administered parenterally by intravenous injection, intramuscular injection or subcutaneous injection, or administered orally after enclosing them in capsules.

The invention will be further illustrated by non-limitative following examples.

EXAMPLE 1

Compounds A and C were tested for the inhibitory effect on tumor metastasis.

Experimental animal: male C57BL/6 mice (6 weeks old)

Tumor cell line: B16-F10 melanoma

Test method: Mice were given $4 \times 10^5$ B16-F10 melanoma cells in 0.05 ml of serum-free RPMI 1640 medium in the foot pad of the left hind leg. A suspension of Compound A or C (0.1 or 0.2 mg) in 0.2 ml of physiological saline containing 1% dimethylsulfoxide was administered intraperitoneally every other day from day 1 to day 27 after inoculation of the melanoma cells. During this period, the size of the inoculated tumor was observed macroscopically. On day 28, tumor-bearing legs were cut from the mice and on day 42 the mice were sacrificed. The number of metastatic nodules formed on the lung surface was counted for each mouse. The results are shown in Table 1. 10 Animals were used per each group

TABLE 1

| Compound | Dose (mg/kg) | Number of metastatic nodules mean ± standard error | Inhibition of metastasis (%) |
|---|---|---|---|
| Control | — | 20.4 ± 15.4 | — |
| A | 10 | 3.0 ± 1.9 | 85 |
| C | 5 | 1.2 ± 0.8 | 94 |
| C | 10 | 0 | 100 |

EXAMPLE 2

Compounds G and H were tested for the inhibitory effect on tumor metastasis. The same experimental animal, tumor cell line and test method as in Example 1 were used except that a suspension of Compound G or H instead of Compound A or C was administered. The inhibitory effect of Compounds G and H was essentially the same as that of Compound C.

EXAMPLE 3

Compounds B, D, E and F were tested for the inhibitory effect on tumor metastasis using the same experimental animal and tumor cell line as in Example 1. Test method: Mice were given $4 \times 10^5$ B16-F10 melanoma cells in 0.05 ml of serum-free RPMI 1640 medium in the foot pad of the left hind leg. A solution of Compounds B, D, E or F (0.1 or 0.2 mg) in 0.2 ml of olive oil was administered intraperitoneally every other day from day 1 to day 27 after inoculation of the melanoma cells. During this period, the size of the inoculated tumors was observed macroscopically. On day 28, the tumor-bearing legs were cut from the mice and on day 42 the mice were sacrificed. The number of metastatic nodules formed on the lung surface was counted for each mouse. 10 Animals were used per each group except for control group wherein 20 animals were used. The results obtained are shown in Table 2.

TABLE 2

| Compound | Dose (mg/kg) | Number of metastatic nodules mean ± standard error | Inhibition of metastasis (%) |
|---|---|---|---|
| Control | — | 31.9 ± 19.8 | — |
| B | 10 | 11.7 ± 6.2 | 63 |
| D | 10 | 5.2 ± 3.4 | 84 |
| E | 5 | 4.8 ± 1.5 | 85 |
| E | 10 | 1.0 ± 0.7 | 97 |
| F | 10 | 12.0 ± 5.9 | 62 |

As evident from the data set forth in Tables 1 and 2, Compounds A–F exhibit excellent inhibitory effect on metastasis of melanoma. Particularly, the administration of 10 mg/Kg of Compound C prevented metastasis by 100% as shown in Table 1. Such inhibitory effect is not the reflection of an inhibitory effect on the growth of tumor itself, because the administration of 10 mg/Kg of Compound B, D or F, or 5 mg/Kg of Compound E also inhibited metastasis in spite of the fact that the growth of the inoculated tumors was about the same as that of Control.

EXAMPLE 4

Compounds A, B, C, D, E and F were tested for the effect on the L-PHA-sensitivity of cultured tumor cell. Tumor cell culture: B16-F10 melanoma cells were incubated in RPMI 1640 medium containing 10% fetal bovine serum and antibiotics at 37° C.

Test method: B16-F10 cells ($5 \times 10^4$) in 2 ml of the medium were seeded onto a plastic dish and incubation was started. On day 1, 10 μl of dimethylsulfoxide (control group) or a test compound suspended in 10 μl of dimethylsulfoxide at a concentration of 50 μg/ml (test group) was added. On day 2, 50 μl each of water was added to a half of each of the control group and the test group, and 50 μl of 50 μg/ml L-PHA solution in water was added to a remaining half. On day 4, the number of cells was counted in L-PHA-treated and untreated groups and % growth inhibition by L-PHA was calculated according to the following formula:

% Growth Inhibition=$(1-N/N_0)\times 100$ in which N denotes a number of cells in the presence of L-PHA and $N_0$ denotes a number of cells in the absence thereof.

TABLE 3

| Compound | Growth inhibition by L-PHA (%) |
| --- | --- |
| Control | 42.0* |
| A | 38.9 |
| B | 36.6 |
| C | 32.7 |
| D | 36.7 |
| E | 31.9 |
| F | 35.2 |

*Mean value obtained from 2 or more experiments

As shown in Table 3, the addition of Compounds A-F reduced the growth inhibition of cells caused by L-PHA in various degrees in comparison with control. This means that all of Compounds A-F achieved reduction in L-PHA-sensitivity of B16-F10 cell line or reduction in GlcNAcβ1-6Man structure.

EXAMPLE 5

An oily emulsion containing Compound A, B, C, G or H was prepared, respectively. Soybean oil (50 g), soybean lecithin (6 g), glycerol (12.5 g) and Compound A, B, C, G or H (each 2.5 g) were mixed and heated at 50°-60° C., and distilled water (250 ml) was added. The resultant mixture was homogenized in a mixer to prepare a crude emulsion. Further amount of distilled water necessary to make the volume to 500 ml was added to the crude emulsion and the whole was introduced into the cistern of Manthon-Gholin high pressure emulsifier and circulated to prepare a homogeneous oily emulsion. The oily emulsions thus obtained containing Compound A, B, C, G or H had a mean particle size of not more than 200 nm. This particle size was maintained after storage of the emulsions for 3 months at about 4° C.

EXAMPLE 6

An oily emulsion containing Compound C or G was prepared using soybean oil (20 g), egg yolk lecithin (2.4 g) and Compound C or G (0.8 g) according to the procedure of Example 4. The emulsion obtained had the same particle size and stability as in Example 5.

EXAMPLE 7

An oily emulsion containing Compound F was prepared using soybean oil (20 g), egg yolk lecithin (2.4 g), sodium palmitate (0.09 g), glycerol (5 g) and Compound F (0.5 g) according to the procedure of Example 5. The emulsion obtained had a mean particle size of not more than 300 nm and this particle size was maintained after storage of the emulsion for 3 months at about 4° C.

EXAMPLE 8

An oily emulsion containing Compound A, B or C, respectively as prepared in Example 5 was tested for the inhibition of tumor metastasis.

Male C57BL/6 mice (6 weeks old) were given $4 \times 10^5$ B16-F10 melanoma cells in 0.05 ml of serum-free RPMI 1640 medium in the foot pad of the left hind leg. A control oily emulsion was prepared as stated in Example 5 in the absence of Compound A, B or C. The control emulsion and the oily emulsions containing Compound A, B or C with a final concentration of 0.03-0.2 mg/ml were administered intravenously in the tail vein 9 times every three days from day 1 to day 25 after inoculation. The tumor-bearing legs were cut on day 27 and the mice were sacrificed on day 41. The number of metastatic nodules formed in the lung was counted for each mouse. 10 Animals were used per each group. % Inhibition of tumor metastasis to lung was calculated on the basis of the following formula.

% Inhibition of tumor metastasis to lung=$(1-M/M_0)\times 100$ in which M denotes an average number of metastatic nodules formed in mice to which were administered the oily emulsions containing Compound A, B or C and $M_0$ denotes an average number of metastatic nodules formed in mice to which was administered the control oily emulsion.

TABLE 4

| Compound | Dose (mg/kg) | Inhibition of tumor metastasis to lung (%) |
| --- | --- | --- |
| C | 0.3 | 79 |
| C | 0.8 | 78 |
| C | 2.0 | 85 |
| A | 0.8 | 67 |
| B | 0.8 | 54 |

As shown in Table 4, the oily emulsions of the invention remarkably inhibited metastasis of tumor cells to lung as compared with the control oily emulsion.

What is claimed is:

1. An oily emulsion for the inhibition of lung metastasis in a mammal which comprises an an active ingredient an effective amount to inhibit lung metastasis of one or more of polyprenols and polyprenyl phosphates of the formula

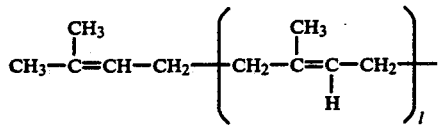

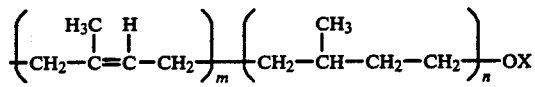

wherein

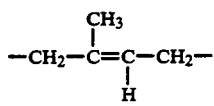

represents a trans-isoprene unit,

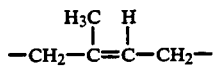

represents a cis-isoprene unit,

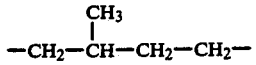

represents a dihydroisoprene unit, l is an integer of 2 to 8, m is 0 or an integer of 5 to 18, n is 0 or 1, the sum of l and m is the range of 8 to 20, X represents a hydrogen atom or $-PO_3MM'$ wherein M and M' may be the same or different and each is a hydrogen atom or a monovalent cation or both M and M' together form a divalent cation.

2. An oily emulsion of claim 1 wherein the active ingredient is solanesyl phosphate diammonium salt.

3. An oily emulsion of claim 1 wherein the active ingredient is α-dihydrodecaprenol.

4. An oily emulsion of claim 1 wherein the active ingredient is α-dihydrodecaprenyl phosphate.

5. An oily emulsion of claim 1 wherein the active ingredient is α-dihydrodecaprenyl phosphate diammonium salt.

6. An oily emulsion of claim 1 wherein the active ingredient is mixed polyprenols having 45 to 60 carbons.

7. An oily emulsion of claim 1 wherein the active ingredient is mixed α-dihydropolyprenols having 50 to 65 carbons.

8. An oily emulsion of claim 1 wherein the active ingredient is mixed dolichyl phosphate diammonium salts having 75 to 110 carbons.

* * * * *